United States Patent [19]
Rink et al.

[11] Patent Number: 5,656,590
[45] Date of Patent: Aug. 12, 1997

[54] TREATMENT OF ANOREXIA AND RELATED STATES

[75] Inventors: Timothy J. Rink, La Jolla; Andrew A. Young, San Diego, both of Calif.

[73] Assignee: Amylin Pharmaceuticals, Inc., San Diego, Calif.

[21] Appl. No.: 157,003

[22] PCT Filed: May 23, 1992

[86] PCT No.: PCT/US92/04357

§ 371 Date: Nov. 24, 1993

§ 102(e) Date: Nov. 24, 1993

[87] PCT Pub. No.: WO92/20367

PCT Pub. Date: Nov. 26, 1992

Related U.S. Application Data

[63] Continuation-in-part of Ser. No. 862,500, Apr. 3, 1992, abandoned, which is a continuation-in-part of Ser. No. 704,995, May 24, 1991, abandoned.

[51] Int. Cl.$^6$ .................. A61K 38/28; C07K 5/00
[52] U.S. Cl. .................. 514/3; 514/4; 514/12; 530/303
[58] Field of Search ............ 514/3, 4, 12; 530/303

[56] References Cited

U.S. PATENT DOCUMENTS

| | | | |
|---|---|---|---|
| 4,985,242 | 1/1991 | Sekine et al. | 424/85.4 |
| 4,988,512 | 1/1991 | Azira | 424/422 |
| 4,992,417 | 2/1991 | Katsoyanimis et al. | 514/3 |
| 4,992,418 | 2/1991 | Katsoyanimis et al. | 514/3 |
| 5,008,241 | 4/1991 | Markussen et al. | 514/3 |
| 5,016,643 | 5/1991 | Applegate et al. | 128/745 |
| 5,028,586 | 7/1991 | Balschmidt et al. | 514/3 |
| 5,028,587 | 7/1991 | Dorschug et al. | 514/3 |
| 5,049,547 | 9/1991 | Hruby et al. | 514/4 |
| 5,124,314 | 6/1992 | Cooper | 514/4 |
| 5,234,906 | 8/1993 | Young et al. | 514/12 |

FOREIGN PATENT DOCUMENTS

| | | |
|---|---|---|
| 0289287 | 11/1988 | European Pat. Off. |
| 0309100 | 3/1989 | European Pat. Off. |
| 0408284 | 1/1991 | European Pat. Off. |
| 0408294 | 1/1991 | European Pat. Off. |

OTHER PUBLICATIONS

Piazza et al, *Comp. Psychiatry*, vol. 21, No. 3, pp. 177–189, May/Jun. 1980.
Ballot et al, *S. Afr. Med. J.*, vol. 59, pp. 992–993, 1981.
Carswell: et al., *Proc. Natl Acad. Sci. U.S.A.* 72:3666–3670, (1976).
Crisp et al., *Br. J. Psychiatry* 128:549, (1976).
Piazza et al., *Compr. Psychiatry* 21:177–189, (1980).
Rouzer & Cerami, *Mol. Biochem. Parasitol.* 2:31–38, (1980).
Ballot et al., *S.Afr. Med. J.* 59:992, (1981).
Goodman and Gilman's *The Pharmaceutical Basis of Therapeutics*, 7th ed., Maxmillan Pub. Co., p. 1501 et seg. (1985).
Cerami et al., *Recent Prog. Horm. Res.* 43:99–112, 1987.
Carmona & Freedland, *J. Nutr.* 119:1304, 1989.
Howard, In: *Harrison's Principals of Internal Medicine* 12th Edition, Wilson et al. (eds) McGraw-Hill, New York, p. 427 (1991).
*BioWorld Today*, vol. 2, No. 125, p. 1, 1991.
Carmona et al, *J. Nutr.*, vol. 119, p. 1304, 1989.
Rouzer et al, *Mol. Biochem. Parasitol.*, vol. 2, pp. 31–38, 1980.

Primary Examiner—Cecilia J. Tsang
Assistant Examiner—Abdel A. Mohamed
Attorney, Agent, or Firm—Lyon & Lyon; Bradford J. Duft

[57] ABSTRACT

Method for treatment of a patient suffering from anorexia or a related condition by administering amylin or an analogue thereof and/or to the patient in an amount sufficient to increase amylin and/or insulin levels in the plasma of the patient.

15 Claims, No Drawings

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
    ( A ) LENGTH: 37 amino acids
    ( B ) TYPE: amino acid
    ( D ) TOPOLOGY: linear ( i x ) FEATURE:
    ( A ) NAME/KEY: Modified-site
    ( B ) LOCATION: 1
    ( D ) OTHER INFORMATION: /note= "residue #1 is hydrogen Lys,
         Ser, Ala, des-alpha-amino Lys, or acetylated Lys"

( i x ) FEATURE:
    ( A ) NAME/KEY: Modified-site
    ( B ) LOCATION: 2
    ( D ) OTHER INFORMATION: /note= "res. #2/independently
         selected residue with side chains chemically
         bonded to res. #7 to form intramolecular linkage"

( i x ) FEATURE:
    ( A ) NAME/KEY: Modified-site
    ( B ) LOCATION: 7
    ( D ) OTHER INFORMATION: /note= "res. #7/independently
         selected residue with side chains chemically
         bonded to res. #2 to form intramolecular linkage"

( i x ) FEATURE:
    ( A ) NAME/KEY: Modified-site
    ( B ) LOCATION: 13
    ( D ) OTHER INFORMATION: /note= "residue #13 is Ala, Ser or
         Thr"

( i x ) FEATURE:
    ( A ) NAME/KEY: Modified-site
    ( B ) LOCATION: 17
    ( D ) OTHER INFORMATION: /note= "residue #17 is Val, Leu or
         Ile"

( i x ) FEATURE:
    ( A ) NAME/KEY: Modified-site
    ( B ) LOCATION: 18
    ( D ) OTHER INFORMATION: /note= "residue #18 is His or Arg"

( i x ) FEATURE:
    ( A ) NAME/KEY: Modified-site
    ( B ) LOCATION: 19
    ( D ) OTHER INFORMATION: /note= "residue #19 is Ser or Thr"

```
    ( i x ) FEATURE:
            ( A ) NAME/KEY: Modified-site
            ( B ) LOCATION: 20
            ( D ) OTHER INFORMATION: /note= "residue #20 is Ser, Thr,
                    Gln or Asn"

( i x ) FEATURE:
            ( A ) NAME/KEY: Modified-site
            ( B ) LOCATION: 21
            ( D ) OTHER INFORMATION: /note= "residue #21 is Asn, Glu or
                    His"

( i x ) FEATURE:
            ( A ) NAME/KEY: Modified-site
            ( B ) LOCATION: 23
            ( D ) OTHER INFORMATION: /note= "residue #23 is Phe, Leu or
                    Tyr"

( i x ) FEATURE:
            ( A ) NAME/KEY: Modified-site
            ( B ) LOCATION: 25
            ( D ) OTHER INFORMATION: /note= "residue #25 is Ala or Pro"

( i x ) FEATURE:
            ( A ) NAME/KEY: Modified-site
            ( B ) LOCATION: 26
            ( D ) OTHER INFORMATION: /note= "residue #26 is Ile, Val,
                    Ala or Leu"

( i x ) FEATURE:
            ( A ) NAME/KEY: Modified-site
            ( B ) LOCATION: 28
            ( D ) OTHER INFORMATION: /note= "residue #28 is Ser, Pro,
                    Leu, Ile or Thr"

( i x ) FEATURE:
            ( A ) NAME/KEY: Modified-site
            ( B ) LOCATION: 29
            ( D ) OTHER INFORMATION: /note= "residue #29 is Ser, Pro or
                    Thr"

( i x ) FEATURE:
            ( A ) NAME/KEY: Modified-site
            ( B ) LOCATION: 31
            ( D ) OTHER INFORMATION: /note= "residue #31 is Asn, Asp or
                    Gln"

( i x ) FEATURE:
            ( A ) NAME/KEY: Binding-site
            ( B ) LOCATION: 37
            ( D ) OTHER INFORMATION: /note= "hydroxy, amino, alkylamino,
                    dialkylamino, cycloalkylamino, arylamino,
                    aralkylamino, alkyloxy, aryloxy or aralkyloxy"

( x i ) SEQUENCE DESCRIPTION: SEQ ID NO:1:

Xaa Xaa Asn Thr Ala Thr Xaa Ala Thr Gln Arg Leu Xaa Asn Phe Leu
1               5                   10                  15

Xaa Xaa Xaa Xaa Xaa Asn Xaa Gly Xaa Xaa Leu Xaa Xaa Thr Xaa Val
            20                  25                  30

Gly Ser Asn Thr Tyr
        35
```

TREATMENT OF ANOREXIA AND RELATED STATES

RELATED APPLICATIONS

This application is a 371 of PCT/US 92/04357, filed May 23, 1992, which is a continuation-in-part of U.S. Ser. No. 07/862,500, filed Apr. 3, 1992, now abandoned, which is a continuation-in-part of U.S. Ser. No. 07/704,995, filed May 24, 1991, now abandoned.

BACKGROUND OF THE INVENTION

This invention relates to treatment of anorexia and related states.

Anorexia, defined as the lack or the loss of appetite for food (Dorland's Illustrated Medical Dictionary, 24 edition, W. B. Saunders Company, Philadelphia, 1965) has multiple etiologies. It is commonly associated with cachexia, "a profound and marked state of constitutional disorder, general ill health and malnutrition" [idem]. Common examples of conditions associated with anorexia and cachexia are anorexia nervosa, certain infectious diseases, and malignancy.

Anorexia nervosa is a serious psychiatric disorder affecting predominantly women (94–96%) in the 13–30 age range. Between 1% (Crisp et al., 128 *Br. J. Psychiatry* 549, 1976) and 3% (Ballot et al., 59 *S.Afr. Med. J.* 992, 1981) of young women may be affected. The morbidity and mortality from this condition are considerable. Two years from diagnosis, 4–6% have died and only 50% have achieved a normal weight. There are multiple endocrine and metabolic abnormalities present, most of which are believed to be secondary to the malnutrition. A serious complication of the condition is osteoporosis, which can involve both the spine and peripheral bones. At present there is no specific treatment for anorexia nervosa, although multiple approaches have been tried (Piazza, Piazza & Rollins *Compr. Psychiatry* 21:177–189 1980).

In experimental animals, infection with various agents such as *Mycobacterium bovis* (Carswell: et al. *Proc. Natl. Acad. Sci. U.S.A.* 73:3666–3670 1975) caused the appearance of a blood factor that caused necrosis of tumors in mice (tumor necrosis factor, TNF). In a different line of investigation, an agent produced in response to infection with *Trypanosoma brucei* produced unexpected weight loss an wasting (Rouzer & Cerami *Mol. Biochem. Parasitol* 2:31–38 1980), and was termed cachexin. TNF and cachexin have since been shown to be the same 17kD protein, produced by activated macrophages. It stimulates several aspects of the immune response. Injected into animals, it produces many of the features of cachexia, including anorexia, bone resorption, and the inhibition of fat uptake into adipocytes. It has been proposed that this agent, which might be produced by tumor cells, or as a host response, could account for some of the cachexia of cancer (Cerami et al. *Recent Prog. Horm. Res.* 43:99–112 1987). However, the association of cachexin/TNF with malignancy is the subject of conflicting reports.

Nutritional support via either enteral (via the gut) or parenteral (e.g., intravenous) therapy is indicated in patients unable to take sufficient nutrition by mouth, and who are therefore at risk for the complication of malnutrition. Therapy attempts to maintain anabolism (buildup of body substance stores) and avert catabolism (breakdown). To this end, insulin is commonly added to intravenously infused nutrients. Examples of patients requiring parenteral nutrition or other nutritional support include those with inflammatory bowel diseases, patients with resected bowel, severe preoperative malnutrition and acute pancreatitis (Howard, In: *Harrison's Principals of Internal Medicine* 12th Edition, Wilson et al. (eds) McGraw-Hill, N.Y. 1991, p. 429).

Human diabetics are deficient in insulin secretion, and in some cases lack insulin. Insulin is one of several hormones which play a role in regulation of blood glucose levels. Simplistically, there are two main stores of glucose in a mammal—the liver and skeletal muscle, where glucose is stored in the form of glycogen. Muscle glycogen is used as a glucose source for the muscle, whereas liver glycogen is used as a glucose source for all tissues, including blood. It is the interplay of certain hormones in regulation of glycogen accumulation and breakdown that is critical in the invention described below.

Insulin regulates glucose uptake by muscle tissue for storage of the glucose as muscle glycogen. Insulin also prevents hyperglycemia, that is, the unacceptable accumulation of high levels of glucose in the blood, and suppresses conversion of liver glycogen to glucose, and subsequent secretion of that glucose into the blood. In the presence of excess insulin, blood glucose accumulates in muscle tissue as glycogen, liver glucose output is suppressed, and the level of blood glucose falls, to create a condition termed hypoglycemia.

Another hormone, glucagon, increases blood glucose levels by stimulating liver glycogen breakdown to glucose, and subsequent secretion of that glucose. This liver glycogen is used to maintain blood glucose levels, and glucagon may be considered an insulin counterregulatory hormone.

Amylin is another hormone which has been discovered to be concerned in regulation of blood glucose levels. It reverses insulin-mediated suppression of liver glucose output in rats. Molina et al., 39 *Diabetes* 260, 1990, and Koopmans et al., 39 *Diabetes* 101A, 1990.

European Patent Application No. 88307927.9 describes the treatment of diabetes mellitus or hypoglycemia with amylin, or with a combination of amylin and insulin, preferably at a ratio of between 100:1 to 0.1:1 insulin to amylin.

SUMMARY OF THE INVENTION

Applicants have discovered that a patient suffering from anorexia may have fasting plasma amylin and insulin concentrations below the normal range, and in fact near the range measured by Type 1 diabetics. Applicants believe that patients suffering from cachexia or receiving parenteral nutrition (i.e., nutrition except oral nutrition, e.g., intravenous) have reduced amylin and/or insulin levels. Thus, applicants propose that patients suffering from anorexia and cachectic states, as well as patients undergoing parenteral nutrition, be administered amylin with or without insulin. Such administration will preferably increase adipose tissue in such patients and thus be of significant benefit. The amount of the hormones (amylin or amylin and insulin) that are administered should preferably be sufficient to increase the hormone plasma levels of the patient to normal levels observed in the general population. For example, in a patient having a level of insulin similar to that in a Type 1 diabetic, it is necessary to administer about 1 mg per day of amylin, alone or with insulin together in a ratio of amylin to insulin between 1:100 and 10:1.

Thus, in a first aspect the invention features a method for treatment of a patient suffering from anorexia by administering amylin or an agonist analogue thereof to the patient in an amount sufficient to increase the amylin level in the plasma of the patient.

In related aspects, the invention features methods for treatment of cachectic patients and those undergoing parenteral nutrition by similarly administering amylin or an agonist analogue thereof in an amount sufficient to increase the amylin plasma level.

In preferred embodiments of the above aspects, the invention features co-administering insulin to the patient in an amount sufficient to increase insulin plasma level; and the amylin (or agonist analogue) and insulin are provided in an amount sufficient to increase the level of adipose tissue in the patient. For example, the amount of amylin or agonist analogue provided is sufficient to increase liver glycogen stores. Insulin and amylin in the patient will act together to enhance the deposition of body fat. Insulin will enhance the uptake of glucose into fat cells and will enhance the transfer of lipid into fats cells via activation of lipoprotein lipase at adipose tissue capillaries. Amylin will enhance the hepatic supply of lactate, a favored lipogenic substrate (Carmona & Freedland 119 *J. Nutr.* 1304, 1989).

In another related aspect, the invention features a method for treating a patient that is deficient in adipose tissue by administering amylin (or an agonist analogue thereof) and/or insulin as described above in an amount sufficient to increase the amount of adipose tissue in that patient. Those in the art will recognize that standard procedures can be used to measure the increase in such adipose tissues, and to identify those patients which are deficient in adipose tissue levels.

In preferred embodiments, the method includes the step of identifying a mammal having the above-noted conditions, prior to the administering step.

In other preferred embodiments, combinations of amylin and insulin are provided in a molar ratio between about 1:2.5 and 1:35 or about 1:5 and 1:25, and at least 0.5 micrograms of amylin per kilogram of the patient per day are provided.

The level of insulin and amylin in the patient may be determined by any desired means, many examples of which exist in the published literature. In addition, amylin activity can be assayed as described by Cooper and Young U.S. Ser. No. 07/666,512, entitled "Amylin Activity Assays", filed Mar. 8, 1991, assigned to the same assignee as the present application, and hereby incorporated by reference herein.

Preferably, where amylin and insulin are administered rather that amylin alone, the composition includes an amylin and an insulin in a molar ratio of between about 1:2.5 and 1:35, preferably in a form which allows delayed release of both the insulin and amylin in a constant molar ratio, or in a form suitable for parenteral administration.

In a related aspect, the treatment may include administering a composition containing an insulin and an amylin at a suitable molar ratio, such that the amount of amylin in the composition will result in circulating plasma levels of amylin that are about 3 to about 6% that of insulin upon administration of the composition to the patient. The contents of U.S. Ser. No. 07/704,995, filed May 24, 1991, are hereby incorporated by reference.

The term "amylin" is used in this application to include compounds defined by Young et al., U.S. application Ser. No. 07/640,478, filed Jan. 10, 1991, now U.S. Pat. No. 5,234,906, entitled "Hyperglycemic Compositions", which (including drawings) is hereby incorporated by reference. For example, it includes the peptide hormone, and species variations of it, referred to as amylin which is synthesized and secreted from the beta cells of the pancreas. Thus, it includes human amylin, cat amylin, dog amylin; rat amylin, mouse amylin, hamster amylin, and guinea pig amylin. Preferably the amylin has an $EC_{50}$ of less than 1 nM in the rat soleus muscle assay as described in, for example, European Patent Application 88307927.9. Amylin functions along with insulin, which is stored and released from the same pancreatic beta cells, to regulate fuel metabolism. Amylin acts through receptors located in skeletal muscle to increase glycogen turnover in this tissue, believed to result in an increased return to the bloodstream of lactate, which is a major precursor of hepatic gluconeogenesis. Amylin cosecretion with insulin after meals therefore results in restoration of hepatic glycogen content and limits the potential which would otherwise exist for insulin to induce hypoglycemia. Administration of amylin to anesthetized rats produces large increases in blood lactate levels, presumably through a direct effect upon skeletal muscle glycogen breakdown and glycolysis. Increased blood lactate content is followed rapidly by increased blood glucose levels, believed to result from provision of gluconeogenic precursors in the form of lactate to the liver. These physiological and pharmacological effects of amylin form the basis for its therapeutic indications in treatment of Type 1 diabetes and hypoglycemia.

The term "amylin analogue" or "agonist analogue" includes derivatives of amylin or other reagents acting as agonists at an amylin receptor, or having those biological properties described above.

The term "analogue" is meant to include human amylin equivalents known to those of ordinary skill in the art. For example, various amino acids in the amylin sequence can be substituted with equivalent amino acids in a manner which has little (i.e., reduces activity less than 20%) or no effect on the biological activity of the amylin, as measured in the assay described above. For example, neutral amino acids can be replaced with other neutral amino acids, and charged amino acids replaced with equivalently charged amino acids. In addition, one or more amino acids may be deleted from the polypeptide if such deletion has little or no affect on the biological activity of the human amylin.

Useful analogues include agonist analogues identified in copending and commonly assigned U.S. Ser. No. 07/794, 266 filed Nov. 19, 1991, the contents of which is hereby incorporated by reference. In particular, useful analogues include agonist analogues having the following sequence:

$^1A_1$-X-Asn-Thr-$^5$Ala-Thr-Y-Ala-Thr-$^{10}$Gln-Arg-Leu-$B_1$-Asn-$^{15}$Phe-Leu-$C_1$-$D_1$-$E_1$-$^{20}F_1$-$G_1$-Asn-$H_1$-Gly-$^{25}I_1$-$J_1$-Leu-$K_1$-$L_1$-$^{30}$Thr-$M_1$-Val-Gly-Ser-$^{35}$Asn-Thr-Tyr-Z wherein $A_1$ is hydrogen Lys, Ser, Ala, des-α-amino Lys, or acetylated Lys; $B_1$ is Ala, Ser or Thr; $C_1$ is val, Leu or Ile; $D_1$ is His or Arg; $E_1$ is Ser or Thr; $F_1$ is Ser, Thr, Gln or Asn; $G_1$ is Asn, Gln or His; $H_1$ is Phe, Leu or Tyr; $I_1$ is Ala or Pro; $J_1$ is Ile, Val, Ala or Leu; $K_1$ is Ser, Pro, Leu, Ile or Thr; $L_1$ is Ser, Pro or Thr; $M_1$ is Asn, Asp or Gln; X and Y are independently selected residues having side chains which are chemically bonded to each other to form an intramolecular linkage; and Z is hydroxy, amino, alkylamino, dialkylamino, cycloalkylamino, arylamino, aralkylamino, alkyloxy, aryloxy or aralkyloxy; provided that (a) when $A_1$ is Lys, $B_1$ is Ala, $C_1$ is Val, $D_1$ is His, $E_1$ is Ser, $F_1$ is Ser, $G_1$ is Asn, $H_1$ is Phe, $I_1$ is Ala, $J_1$ is Ile, $K_1$ is Ser, $L_1$ is Ser, and $M_1$ is Asn; (b) when $A_1$ is Lys, $B_1$ is Ala, $C_1$ is Ile, $D_1$ is Arg, $E_1$ is Ser, $F_1$ is Ser, $G_1$ is Asn, $H_1$ is Leu, $I_1$ is Ala, $J_1$ is Ile, $K_1$ is Ser, $L_1$ is Pro, and $M_1$ is Asn; (c) when $A_1$ is Lys, $B_1$ is Ala, $C_1$ is Val, $D_1$ is Arg, $E_1$ is Thr, $F_1$ is Ser, $G_1$ is Asn, $H_1$ is Leu, $I_1$ is Ala, $J_1$ is Ile, $K_1$ is Ser, $L_1$ is Pro, and $M_1$ is Asn; (d) when $A_1$ is Lys, $B_1$ is Ala, $C_1$ is Val, $D_1$ is Arg, $E_1$ is Ser, $F_1$ is Ser, $G_1$ is Asn, $H_1$ is Leu, $I_1$ is Pro, $J_1$ is Val, $K_1$ is Pro, $L_1$ is Pro, and $M_1$ is Asn; (e) when $A_1$ is Lys, $B_1$ is Ala, $C_1$ is Val, $D_1$ is His, $E_1$ is Ser, $F_1$ is Asn, $G_1$ is Asn, $H_1$ is Leu, $I_1$ is Pro, $J_1$ is Val, $K_1$ is Ser, $L_1$ is Pro and $M_1$ is Asn; or (f) when $A_1$ is Lys, $B_1$ is Thr, $C_1$ is Val, $D_1$ is Arg, $E_1$ is Ser, $F_1$ is Ser, $G_1$ is His, $H_1$ is Leu, $I_1$ is Ala, $J_1$ is Ala, $K_1$ is Leu, $L_1$ is Pro and $M_1$ is Asp; then one or more of any of $A_1$ to $M_1$ is not an L-amino acid and Z is not amino.

Suitable side chains for X and Y include groups derived from alkyl sulfhydryls which may form disulfide bonds; alkyl acids and alkyl amines which may form cyclic lactams; alkyl aldehydes or alkyl halides and alkylamines which may condense and be reduced to form an alkyl amine bridge; or side chains which may be connected to form an alkyl, alkenyl, alkynyl, ether or thioether bond. Preferred alkyl chains include lower alkyl groups having from about 1 to about 6 carbon atoms.

The term "alkyl" refers to both straight- and branched-chain alkyl groups. The term "lower alkyl" refers to both straight- and branched-chain alkyl groups having a total of from 1 to 6 carbon atoms and includes primary, secondary and tertiary alkyl groups. Typical lower alkyls include, for example, methyl, ethyl, n-propyl, isopropyl, n-butyl, isobutyl, t-butyl, n-pentyl, n-hexyl, and the like.

The term "aryl" refers to carbocyclic aromatic groups of 6 to 14 carbon atoms such as phenyl and naphthyl, as well as heterocyclic aromatic groups containing 1 to 3 heteroatoms (nitrogen, oxygen, sulfur, etc.) such as pyridyl, triazolopyrazine, pyrimidine and the like.

The term "aralkyl" refers to an "aryl" group of 6 to 10 carbon atoms directly attached to an "alkyl" group of 1 to 4 carbon atoms and includes for example benzyl, p-chlorobenzyl, p-methylbenzyl, and 2-phenylethyl.

The term "cycloalkyl" refers to cyclic alkyl groups of 5 to 8 carbon atoms.

By "identifying" is meant to include noting the symptoms or characteristics of anorexia or cachectic conditions. Such symptoms are well known in the art. It also includes chemical or biochemical assays which indicate such conditions, or their equivalent.

By "insulin" is meant a polypeptide or its equivalent useful in regulation of blood glucose levels. A general description of such insulins is provided in Goodman and Gilman, "The pharmacological basis of therapeutics, 7th ed., Maxmillan Pub. Co. at e.g., p. 1501, et seq. (1985). Such insulins can be fast acting, intermediate acting, or long acting. Id. at 1502. Various derivatives of insulin exist and are useful in this invention. See e.g., U.S. Pat. Nos., 5,049, 547, 5,028,587, 5,028,586, 5,016,643. Insulin peptides are also useful (see, e.g., U.S. Pat. No. 5,008,241), as are analogues (see e.g., U.S. Pat. No. 4,992,417 and 4,992,418). Such insulin can be administered by any standard route, including nasal administration, see e.g., U.S. Pat. Nos. 4,988,512 and 4,985,242, and 2 BioWorld Today, No. 125, 1, 1991.

Other features and advantages of the invention will be apparent from the following description of the preferred embodiments thereof, and from the claims.

DESCRIPTION OF THE PREFERRED EMBODIMENTS

Fat Deficient Conditions

Conditions such as anorexia nervosa, cachectic conditions and the general condition of patients receiving intravenous nutrition or other related conditions may be treated in this invention. In each of these conditions there is either progressive loss of both adipose tissue and lean body mass or failure to increase these from a base of marked established loss.

Applicants has found that amylin is a controller of fuel cycling from muscle to liver and liver to peripheral tissues. Without being bound to any particular theory, applicant believes that this is due, at least in some part, to promotion of Cori cycling of carbohydrate from skeletal muscle glycogen to liver glycogen and by the provision of hepatic substrate for triglyceride synthesis. Applicants believes that activation of these pathways improves the efficient storage of food-derived substrates in liver and in adipose tissue in the above-exemplified conditions. Thus, the combined use of amylin and insulin in which amylin serves to provide hepatic substrate and insulin promotes hepatic production of triglyceride and lipogenesis in adipose tissue is beneficial.

Promotion of formation of adipose tissue is critical to normal health not only as a concentrated store of energy for use in fasting or exercise, but subcutaneous fat especially is important in establishing the body contours and cushioning of the underlying tissues. Bed sores, for example, may be caused or exacerbated by loss of adipose tissue.

Amylin deficiency in Type 1 diabetics has been proposed as a pathologic basis for difficulties in achieving good glycemic control with insulin therapy. Applicants has discovered that an anorexic patient has fasting plasma amylin and insulin concentrations below the normal range, and in fact near the range measured in Type 1 diabetics. When such a patient was administered a standard 75 g glucose oral load there was a very small transient deviation of amylin and insulin levels, markedly lower than that seen in normal subjects. Thus, it appears that anorexia nervosa is an amylin, and possibly insulin, deficient state which can be treated by administration of amylin and/or insulin.

While this proposal is counter to reports that amylin can suppress appetite (which is clearly an undesirable feature for treatment of anorexia or cachectic states), applicant believes that the appetite suppressant effects of amylin is seen only at very high doses and may be short lived. Indeed, applicant has discovered that in toxicological studies with amylin in both rats and dogs, where two weeks of amylin administration were used, there was no reduction in food intake or weight in the animal.

As with anorexia, applicant believes that both cachectic states and patients receiving total parenteral nutrition are amylin and/or insulin deficient states and thus, appropriate for amylin replacement or augmentation therapy.

Compositions

Compositions or products according to the invention may conveniently be provided in the form of solutions suitable for parenteral or nasal or oral administration. In many cases, it will be convenient to provide an amylin or insulin in a single solution for administration together. In other cases, it may be more advantageous to administer amylin and insulin separately. A suitable administration regime may best be determined by a doctor for each patient individually. It will generally be preferable to formulate such that the molar ratio of amylin and insulin for the treatment is between 1:100 and 10:1, or between 1:2.5 and 1:35. Most preferably between 1:25 or 1:20 and 1:5.

Since the products of the invention are amphoteric they may be utilized as free bases, as acid addition salts or as metal salts. The salts must, of course, be pharmaceutically acceptable, and these will include metal salts, particularly alkali and alkaline earth metal salts, e.g., potassium or sodium salts. A wide variety of pharmaceutically acceptable acid addition salts are available. These include those prepared from both organic and inorganic acids, preferably mineral acids. Typical acids which may be mentioned by way of example include citric, succinic, lactic, hydrochloric and hydrobromic acids. Such products are readily prepared by procedures well known to those skilled in the art.

The products of the invention will normally be provided as parenteral compositions for injection or infusion. They can, for example, be suspended in an inert oil, suitably a vegetable oil such as sesame, peanut, or olive oil. Alternatively, they can be suspended in an aqueous isotonic buffer solution at a pH of about 5.6 to 7.4. Useful buffers include sodium citrate-citric acid and sodium phosphate-phosphoric acid.

The desired isotonicity may be accomplished using sodium chloride or other pharmaceutically acceptable agents such as dextrose, boric acid, sodium tartrate, propylene glycol or other inorganic or organic solutes. Sodium chloride is preferred particularly for buffers containing sodium ions.

If desired, solutions of the above compositions may be thickened with a thickening agent such as methyl cellulose. They may be prepared in emulsified form, either water in oil or oil in water. Any of a wide variety of pharmaceutically acceptable emulsifying agents may be employed including, for example acacia powder, or an alkali polyether alcohol sulfate or sulfonate such as a Triton.

The therapeutically useful compositions of the invention are prepared by mixing the ingredients following generally accepted procedures. For example, the selected components may be simply mixed in a blender or other standard device to produce a concentrated mixture which may then be adjusted to the final concentration and viscosity by the addition of water or thickening agent and possibly a buffer to control pH or an additional solute to control tonicity.

For use by the physician, the compositions will be provided in dosage unit form containing an amount of amylin and/or insulin which will be effective in one or multiple doses to control adipose tissue formation at the selected level. As will be recognized by those in the field, an effective amount of therapeutic agent will vary with many factors including the age and weight of the patient, the patient's physical condition, the blood sugar level to be obtained, and other factors. Typical dosage units for treatment of anorexia and related conditions will contain, for example, from about 0.1 to 10 mg of an amylin and about 0.1 to about 1.0 mg of an insulin.

Methods

As defined above, compositions useful in the invention are formulated by standard procedure. These compositions are also administered by standard procedure. Suitable doses are readily determined by those in the art, examples of which are provided above.

Amylin analogues may be prepared by using certain conventional coupling reactions known in the peptide art. The analogues are prepared by successively adding the desired amino acid to a growing peptide chain. Typically, an α-N-carbamoyl protected amino acid and an amino acid attached to the growing peptide chain on a resin support are reacted at room temperature in an inert solvent such as N-methylpyrrolidone, dimethylformamide or methylene chloride in the presence of coupling agents such as dicyclohexylcarbodiimide 1-hydroxybenzotriazole in the presence of a base such as diisopropylethylamine. The α-N-carbamoyl protecting group is removed from the resultant peptide with a reagent such as trifluoroacetic acid or piperidine, and the coupling reaction repeated with the next desired N-protected amino acid. Suitable N-protecting groups are known in the art, with t-butyloxycarbonyl herein preferred.

Certain preferred methods for synthesis are described in the commonly-assigned copending and commonly assigned patent application Ser. No. 667,040 ("Synthetic Preparation of Amylin and Amylin Analogs", filed Mar. 8, 1991). These methods provide for solid phase synthesis of a peptide which comprises amylin or an amylin analogue which has enhanced biological activity and is substantially free of deletion and other contaminating peptides wherein said peptide is synthesized using successive synthesis cycles, whereby in each such synthesis cycle, a designated amino acid is added to a growing peptide chain attached to an insoluble resin support by formation of a peptide linkage between an α-amino group of the growing peptide chain and on α-carboxyl of the designated amino acid; and wherein each synthesis cycle comprises: (a) treating the growing peptide chain under α-amino deprotecting conditions to remove an α-amino group; (b) activating the α-carboxyl group of the α-amino protected designated amino acid; (c) contacting the growing peptide chain and the designated amino acid under coupling conditions to form a peptide linkage between the free α-amino for the peptide chain and the activated α-carboxyl of the designated amino acid; and (d) repeating steps (b) and (c) if the coupling efficiency of step (c) is less than about 97%. It is preferred to repeat steps (b) and (c) if the coupling efficiency is less than about 99%. In another preferred aspect, steps (b) and (c) are repeated in each synthesis cycle. Optionally, the coupling efficiency is measured after each coupling step.

Suitable coupling conditions include use of a solvent system which maximizes swelling of the solid support, minimizes secondary structure elements of the peptide chain during synthesis cycles, and minimizes intrapeptide and interpeptide hydrogen bonding. Preferably the synthesis cycle includes a capping step after the coupling step(s) wherein unreacted α-amino groups of the peptide chain are rendered unreactive. The synthesis cycle is successively repeated using appropriate protected α-amino acids to give amylin or an amylin analogue of specified sequence. After completions of the successive synthesis cycles, said amylin or amylin analogue is cleaved from the solid support. It is preferred that the cysteine residues of the peptide chain are selectively deprotected and an intramolecular disulfide bond is formed before cleaving the peptide bond from the solid support.

Suitable α-amino protective groups include t-butoxycarbonyl and 9-fluorenylmethoxycarbonyl. In one preferred aspect, when t-butoxycarbonyl is used as the α-amino protecting group, the α-carboxyl groups are activated using dicyclohexylcarbodiimide and 1-hydroxybenzotriazole to form 1-hydroxybenzotriazole esters. A particularly preferred solvent system comprise N-methylpyrrolidone.

Amylins and amylin analogues may also be prepared using recombinant DNA techniques, using methods now known in the art. See, e.g., Sambrook et al., *Molecular Cloning: A Laboratory Manual*, 2d Ed., Cold Spring Harbor (1989).

Analogues

Analogues of amylin can be assayed for activity in the soleus muscle assay described above. Amylin agonist activity of compounds may also be assessed by the ability to induce hyperlactemia and/or hyperglycemia in mammals. The preferred analogues des-$^1$Lys-h-amylin, $^{28}$Pro-h-amylin, $^{25,28,29}$Pro-h-amylin, $^{18}$Arg$^{25,28}$Pro-h-amylin, and des-$^1$Lys$^{18}$Arg$^{25,28}$Pro-h-amylin, all show amylin activity in vivo in treated test animals, provoking marked hyperlactemia followed by hyperglycemia. In addition to having activities characteristic of amylin, certain of the preferred compounds also possess more desireable solubility and stability characteristics when compared to human amylin. These preferred compounds include $^{25}$Pro$^{26}$Val$^{28,29}$Pro-h-amylin, $^{25,28,29}$Pro-h-amylin, and $^{18}$Arg$^{25,28}$Pro-h-amylin.

Compounds described herein which are especially preferred include $^{18}$Arg$^{25,28}$Pro-h-amylin, des-$^{1}$Lys$^{18}$Arg$^{25,28}$Pro-h-amylin, $^{18}$Arg$^{25,28,29}$Pro-h-amylin, des-$^{1}$Lys$^{18}$Arg$^{25,28,29}$Pro-h-amylin, $^{25,28,29}$Pro-h-amylin des-$^{1}$Lys$^{25,28,29}$Pro-h-amylin, and $^{25}$Pro$^{26}$Val$^{25,28}$Pro-h-amylin. Still further amylin analogues include:

$^{23}$Leu$^{25}$Pro$^{26}$Val$^{28,29}$Pro-h-amylin;
$^{23}$Leu$^{25}$Pro$^{26}$Val$^{28}$Pro-h-amylin;
des-$^{1}$Lys$^{23}$Leu$^{25}$Pro$^{26}$Val$^{28}$Pro-h-amylin;
$^{18}$Arg$^{23}$Leu$^{25}$Pro$^{26}$Val$^{28}$Pro-h-amylin;
$^{18}$Arg$^{23}$Leu$^{25,28,29}$Pro-h-amylin;
$^{18}$Arg$^{23}$Leu$^{25,28}$Pro-h-amylin;
$^{17}$Ile$^{23}$Leu$^{25,28,29}$Pro-h-amylin;
$^{17}$Ile$^{25,28,29}$Pro-h-amylin;
des-$^{1}$Lys$^{17}$Ile$^{23}$Leu$^{25,28,29}$Pro-h-amylin;
$^{17}$Ile$^{18}$Arg$^{23}$Leu-h-amylin;
$^{17}$Ile$^{18}$Arg$^{23}$Leu$^{26}$Val$^{29}$Pro-h-amylin;
$^{17}$Ile$^{18}$Arg$^{23}$Leu$^{25}$Pro$^{26}$Val$^{28,29}$Pro-h-amylin;
$^{13}$Thr$^{21}$His$^{23}$Leu$^{26}$Ala$^{28}$Leu$^{29}$Pro$^{31}$Asp -h-amylin;
$^{13}$Thr$^{21}$His$^{23}$Leu$^{26}$Ala$^{29}$Pro$^{31}$Asp-h-amylin;
des-$^{1}$Lys$^{13}$Thr$^{21}$His$^{23}$Leu$^{26}$Pro$^{31}$Asp-h-amylin;
$^{13}$Thr$^{18}$Arg$^{21}$His$^{23}$Leu$^{26}$Ala$^{29}$Pro$^{31}$Asp-h-amylin;
$^{13}$Thr$^{18}$Arg$^{21}$His$^{23}$Leu$^{28,29}$Pro$^{31}$Asp-h-amylin; and,
$^{13}$Thr$^{18}$Arg$^{21}$His$^{23}$Leu$^{25}$Pro$^{26}$Ala$^{28,29}$Pro$^{31}$Asp-h-amylin.

Other embodiments are within the following claims.

---

We claim:

1. A method for treatment of a patient suffering from anorexia comprising the step of:
   administering amylin or an analogue thereof to said patient in an amount sufficient to increase the amylin level in the plasma of said patient.

2. A method for treatment of a cachectic patient or a patient undergoing parenteral nutrition comprising the step of:
   administering amylin or an analogue thereof to said patient in an amount sufficient to increase the amylin level in the plasma of said patient.

3. The method of claim 1 wherein said amount of amylin or amylin analogue administered is sufficient to increase the anabolic effect of plasma amylin within the liver, and thereby increase glycogen levels by glycogenesis.

4. The method of claim 1 wherein said amylin is administered in an amount sufficient to enhance mobilization of lactate from muscle to form fat in the liver.

5. The method of claim 1 or 2 wherein said amylin or amylin analogue is provided in an amount sufficient to increase adipose tissue in said patient.

6. The method of claim 1 or 2 further comprising administering insulin to said patient an amount sufficient to increase the insulin level in said patient.

7. The method of claim 6 wherein said amylin and/or said insulin are provided in an amount or amounts sufficient to increase adipose tissue in said patient.

8. A method for treating a patient deficient in adipose tissue comprising administering amylin or an amylin analogue alone or in conjunction with insulin in an amount and ratio sufficient to increase adipose tissue in said patient.

9. A method for treatment of a patient suffering from anorexia comprising administering amylin or an analogue thereof to said patient in an amount sufficient to increase the body weight of said patient.

10. A method for treatment of a cachectic patient or a patient undergoing parenteral nutrition comprising administering to said patient an amount of amylin or an amylin analogue sufficient to reduce the amount of weight loss in said patient.

11. The method of claim 9 wherein said amount of amylin or amylin analog administered is sufficient to increase the anabolic effect of plasma amylin within the liver, and thereby increase glycogen levels by glycogenesis.

12. The method of claim 9 wherein said amylin is administered in an amount sufficient to enhance mobilization of lactate from muscle to form fat in the liver.

13. The method of claim 9 or 10 wherein said amylin or amylin analog is provided in an amount sufficient to increase adipose tissue in said patient.

14. The method of claim 9 or 10 further comprising administering to said patient an amount of insulin sufficient to increase the amount of said insulin in said patient.

15. The method of claim 14 wherein said amylin and/or said insulin are provided in an amount or amounts sufficient to increase adipose tissue in said patient.

* * * * *